US012589036B2

(12) United States Patent
Piantoni et al.

(10) Patent No.: US 12,589,036 B2
(45) Date of Patent: Mar. 31, 2026

(54) COMPOSITE WEB

(71) Applicant: GDM S.p.A., Bologna (IT)

(72) Inventors: Matteo Piantoni, Bologna (IT);
Alessandro Zavalloni, Bologna (IT)

(73) Assignee: GDM S.P.A., Bologna (IT)

( * ) Notice: Subject to any disclaimer, the term of this
patent is extended or adjusted under 35
U.S.C. 154(b) by 843 days.

(21) Appl. No.: 17/852,773

(22) Filed: Jun. 29, 2022

(65) Prior Publication Data

US 2023/0000692 A1 Jan. 5, 2023

(30) Foreign Application Priority Data

Jun. 30, 2021 (IT) ........................ 102021000017126
Jun. 30, 2021 (IT) ........................ 102021000017135

(51) Int. Cl.
*A61F 13/15* (2006.01)
*A61F 13/51* (2006.01)
*A61F 13/512* (2006.01)

(52) U.S. Cl.
CPC .. *A61F 13/15699* (2013.01); *A61F 13/15658*
(2013.01); *A61F 13/15723* (2013.01); *A61F*
*13/15731* (2013.01); *A61F 13/5126* (2013.01);
*A61F 2013/1591* (2013.01)

(58) Field of Classification Search
CPC .......... A61F 13/15699; A61F 13/15658; A61F
13/15723; A61F 13/15731; A61F
13/5126; A61F 2013/1591
See application file for complete search history.

(56) References Cited

U.S. PATENT DOCUMENTS

| | | | | |
|---|---|---|---|---|
| 2,610,629 A | * | 9/1952 | Hawkins | .............. A61B 10/007 |
| | | | | 600/573 |
| 5,591,148 A | | 1/1997 | McFall | |
| 5,607,414 A | * | 3/1997 | Richards | .............. A61F 13/539 |
| | | | | 604/370 |
| 5,620,545 A | | 4/1997 | Braun | |
| 6,311,754 B1 | * | 11/2001 | Marschke | ............ B31F 1/2863 |
| | | | | 156/472 |
| 8,603,277 B2 | | 12/2013 | Paldey | |
| 8,658,852 B2 | * | 2/2014 | Paldey | .................. A61F 13/539 |
| | | | | 604/379 |
| 9,655,790 B2 | * | 5/2017 | Kurihara | ............. A61F 13/5116 |

(Continued)

FOREIGN PATENT DOCUMENTS

| | | |
|---|---|---|
| EP | 3123993 A1 | 2/2017 |
| EP | 3431063 A1 | 1/2019 |

(Continued)

OTHER PUBLICATIONS

Italian Search Report dated Mar. 9, 2022 from counterpart Italian
Patent Application No. 202100017126.

(Continued)

*Primary Examiner* — Guy K Townsend
(74) *Attorney, Agent, or Firm* — SHUTTLEWORTH &
INGERSOLL, PLC; Timothy J. Klima

(57) ABSTRACT

A composite web including a first continuous web having a
first face and a second face; the first web includes a molded
portion having at least one protrusion, at least partly delim-
ited by a base portion, on the first face; the composite web
includes a segment of a second continuous web joined to the
second face of the first web at least at the base portion.

6 Claims, 6 Drawing Sheets

(56) References Cited

U.S. PATENT DOCUMENTS

| | | | | |
|---|---|---|---|---|
| 10,070,999 | B2 * | 9/2018 | Faulks | B32B 5/022 |
| 10,390,999 | B2 * | 8/2019 | Helton | B65H 37/04 |
| 11,134,925 | B2 * | 10/2021 | Barnhorst | A61F 13/513 |
| 11,813,145 | B2 * | 11/2023 | Borrero | A61F 13/4902 |
| 12,075,985 | B2 * | 9/2024 | Barnhorst | A61F 13/49011 |
| 2003/0212376 | A1 * | 11/2003 | Walter | A61F 13/15658 |
| | | | | 442/327 |
| 2007/0179469 | A1 * | 8/2007 | Takahashi | A61F 13/535 |
| | | | | 604/385.101 |
| 2010/0312206 | A1 * | 12/2010 | Fujioka | A61F 13/539 |
| | | | | 604/365 |
| 2014/0000798 | A1 | 1/2014 | Hargett | |
| 2014/0023822 | A1 * | 1/2014 | Tai | B32B 7/05 |
| | | | | 428/116 |
| 2014/0121621 | A1 * | 5/2014 | Kirby | A61F 13/5126 |
| | | | | 604/374 |
| 2015/0283000 | A1 * | 10/2015 | Faulks | B32B 5/022 |
| | | | | 604/385.101 |
| 2015/0290047 | A1 * | 10/2015 | Royce | B32B 41/00 |
| | | | | 156/64 |
| 2016/0075122 | A1 * | 3/2016 | Strube | B32B 5/22 |
| | | | | 156/91 |
| 2016/0128878 | A1 * | 5/2016 | Bonelli | B29C 65/48 |
| | | | | 156/263 |

| | | | | |
|---|---|---|---|---|
| 2017/0079854 | A1 * | 3/2017 | Butler | A61F 13/491 |
| 2017/0079857 | A1 * | 3/2017 | Willhaus | A61F 13/49011 |
| 2018/0368817 | A1 * | 12/2018 | Tally | A61F 13/495 |
| 2019/0076304 | A1 * | 3/2019 | Borrero | A61F 13/49012 |
| 2019/0290505 | A1 * | 9/2019 | Varona | A61F 13/53 |
| 2020/0078231 | A1 * | 3/2020 | Arora | A61F 13/472 |
| 2023/0000692 | A1 * | 1/2023 | Piantoni | A61F 13/15658 |
| 2023/0000693 | A1 * | 1/2023 | Piantoni | D04H 1/559 |
| 2024/0091074 | A1 * | 3/2024 | Borrero | A61F 13/49012 |

FOREIGN PATENT DOCUMENTS

| | | | | |
|---|---|---|---|---|
| WO | WO-2014068488 | A1 * | 5/2014 | A61F 13/51104 |
| WO | 2016040091 | A1 | 3/2016 | |

OTHER PUBLICATIONS

Italian Search Report dated Mar. 9, 2022 from counterpart Italian Patent Application No. 202100017135.

Italian Search Report dated Mar. 9, 2022 from related Italian Patent App 202100017159.

Italian Search Report dated Mar. 9, 2022 from related Italian Patent App 202100017132.

European Search Report dated Jul. 15, 2024 from related European App No. 22180490.9.

* cited by examiner

COMPOSITE WEB

This application claims priority to Italian Patent Application 102021000017135 filed Jun. 30, 2021 and Italian Patent Application 102021000017126 filed Jun. 30, 2021, the entirety of both are incorporated by reference herein.

BACKGROUND OF THE INVENTION

This invention relates to a composite web used to make absorbent sanitary articles, an absorbent sanitary article comprising the composite web, a method for the production of and a unit for forming the composite web.

Generally speaking, absorbent sanitary articles essentially comprise a topsheet, a backsheet and an absorbent core disposed between the topsheet and the backsheet. The topsheet is usually the layer that is in contact with the wearer, while the backsheet is the outer layer of the article.

Known in the prior are absorbent articles, like the one shown, for example, in document WO2016040091A1, which comprise a topsheet comprising what is known as a three-dimensional layer, with bubble-like protrusions obtained by deforming a web using embossing technology; the bubbles allow improving the comfort of the wearer of the absorbent article.

To ensure that the sheet subjected to embossing keeps the desired shape, the topsheet usually also comprises a second layer or base layer joined to the embossed web.

In state-of-the-art products, the absorbent article comprises a liquid acquisition and distribution layer, known as ADL, applied to the topsheet and disposed between the base layer and the absorbent core, that is to say, applied to the base layer on the side opposite the three-dimensional layer.

The ADL allows receiving the liquids to transfer them and direct them towards the absorbent core, thus making more efficient use of the absorbent core.

Disadvantageously, the production of webs for sanitary articles including a topsheet that comprises a three-dimensional layer, a base layer and an ADL applied to the topsheet involves large amounts of material and high production costs.

There is a need to make webs for sanitary articles that are more economical while still ensuring wearer comfort.

SUMMARY OF THE INVENTION

This invention therefore has for an aim to meet the above mentioned need.

At least the aim specified is achieved by a composite web, an absorbent sanitary article comprising the composite web, a method for the production of and a unit for forming the composite web in accordance with the independent claims.

The dependent claims correspond to possible different embodiments of the invention.

According to an aspect, the disclosure relates to a composite web, in particular a composite web used to make absorbent sanitary articles such as, for example, diapers and the like.

According to an aspect, the composite web comprises a first web having a first face and a second face.

According to an aspect, the first face of the composite web is the face that will be in contact with the wearer (for example, when the composite web to make an absorbent sanitary product such as a diaper).

According to an aspect, the first web comprises at least one portion with a pattern stamped on it so that it has at least one protrusion on the first face. Hereinafter, the portion with a pattern stamped on it is also called "molded portion" or "contoured portion". In practice, the contoured portion is a portion of the first web with the aforesaid pattern molded on it.

According to an aspect, the protrusion is at least partly delimited by a base portion.

In broad terms, the protrusion protrudes, relative to the base portion, from the first face towards the wearer to enhance the comfort of the absorbent article which incorporates the composite web.

According to an aspect, the composite web comprises a segment of a second web joined to the second face of the first web at least at the base portion.

According to an aspect, the composite web has at least one cavity delimited by the first web and by the segment of second web at the contoured portion.

According to an aspect, with the protrusion, the segment delimits a cavity in the composite web.

Advantageously, the segment of the second web keeps the molded portion in the deformed state by fixing the first web at least at the molded portion itself.

According to an aspect, the first web is made from non-woven fabric.

According to an aspect, the segment of second web is a liquid acquisition and distribution layer (ADL).

According to an aspect, the segment of second web is made from non-woven fabric.

By "non-woven fabric" is meant a material whose fibers are randomly oriented.

The segment of second web may be made, for example, from: carded fibers, non-woven fabrics, cellulose fibers, viscose, polyester, cotton, polyamide and microfiber.

Advantageously, the segment of second web applied to the first web allows keeping the shape imparted to the first layer.

Advantageously, keeping the shape of the first web using segments of second web instead of a second continuous web allows reducing the amount of material used.

Advantageously, reducing the amount of material used allows lowering production costs.

Advantageously, the presence of an ADL allows acquiring and distributing the liquids that permeate from the first web.

According to an aspect, the molded portion, on its first, face, has a multiplicity of protrusions delimited by base portions.

According to an aspect, the composite web comprises a segment of a second web joined to the second face of the first web at least at the multiplicity of base portions.

According to an aspect, the composite web has a multiplicity of cavities delimited by the first web and by the segment at the molded portion.

Advantageously, the presence of protrusions allows ensuring the wearer's comfort.

According to an aspect, the multiplicity of protrusions defines a motif. In other words, the multiplicity of protrusions defines a pattern on the first web.

According to an aspect, the first web has moldings along its full length. The segments of second web joined to the first web keep the motif or pattern molded on the first web in shape at the segments themselves.

According to an aspect, the first web is molded using embossing technology.

According to an aspect, the composite web comprises a discrete succession of segments of second web.

According to an aspect, the protrusion may have different shapes.

In an example, the protrusion has a bubble shape.

In another example, the protrusion has a wavy shape.

Other examples of shapes that the protrusion may have are the following: circular, diamond, oval, teardrop, elliptical, heart, triangular.

According to an aspect, the molded portion of the first web and the segment of the second web are joined by welding.

For example, welding may be performed using ultrasounds.

According to an aspect, the composite web comprises an adhesive layer to join together the first and the second web.

According to an aspect, the adhesive layer is interposed between the molded portion of the first web and the segment of the second web.

According to an aspect, the segment of the second web has plan dimensions that correspond to the plan dimensions of the molded portion so that the first web keeps the shape or the pattern imparted to it at least in the molded portion.

Advantageously, the dimensions of the segment are determined on the basis of the dimensions of the molded portion.

According to an aspect, the description regards an absorbent article essentially comprising: a topsheet, a backsheet and an absorbent core disposed between the topsheet and the backsheet.

According to an aspect, the topsheet comprises a segment of a composite web according to one or more of the aspects set out above.

According to an aspect, the segment of the second web is disposed between the first web and the absorbent core.

For example, the first web may be made in the form of what is known as a bubble topsheet, that is to say, a topsheet with bubbles on it to enhance the comfort of the wearer.

Advantageously, making an absorbent article whose topsheet has the above mentioned aspects allows reducing the amount of material needed to produce the article. In effect, the segment of web used for the topsheet comprises a molded portion and the ADL at the molded portion to keep it in the desired shape.

Advantageously, reducing the amount of material needed to make the article allows reducing production costs.

According to an aspect, the description regards a method for the production of a composite web (for absorbent sanitary articles).

According to an aspect, the method comprises a step of feeding a first continuous web.

According to an aspect, the method comprises a step of molding the first continuous web to obtain at least one protrusion, delimited at least partly by a base portion.

Advantageously, molding the first web allows making protrusions that improve the comfort of the wearer of the end product comprising the contoured (molded) web.

According to an aspect, the first web can be molded to obtain protrusions with a different shape.

According to an aspect, the first web can be molded to obtain a pattern of protrusions.

According to an aspect, molding is performed using embossing technology.

For example, molding the protrusions can be performed using a first roller that is provided with a plurality of suction hollows on its outer peripheral surface, and a second roller that is peripherally provided with a plurality of teeth that are substantially shaped to match the suction hollows.

According to an aspect, the method comprises a step of joining at least one segment of a second web to the first continuous web at the base portion or base portions on the molded portion.

Advantageously, joining segments of second web to the base portion of the protrusion allows ensuring that the protrusion remains in place.

Advantageously, joining segments of second web to the base portion of the protrusion allows ensuring that the protrusion keeps the shape imparted to the first web at least at the segments of the second web.

According to an aspect, joining at least one segment of second web to the first web allows delimiting at least one cavity between the first continuous web and the segment at the segments of second web.

Advantageously, joining segments of second web allows reducing the amount of material needed for production.

Advantageously, using a smaller amount of material allows reducing production costs.

According to an aspect, the method comprises a step of feeding, cutting and spacing a second continuous web to obtain segments of second web.

According to an aspect, the step of cutting to obtain segments of second web is performed using, for example, the slip and cut method.

According to an aspect, the step of joining at least one segment of a second web to the first continuous web comprises a step of welding at least one segment of second web to the first continuous web.

Welding may be, for example, ultrasound welding.

According to an aspect, the step of joining at least one segment of a second web to the first continuous web comprises a step of disposing an adhesive layer between the at least one segment of second web and the first continuous web.

Joining the segments of the second web to the first web allows fixing and keeping, at least at the segments, the 3D pattern that has been imparted to the first web.

This description also relates to a forming unit for making composite webs according to one or more of the above mentioned aspects.

According to an aspect, the forming unit comprises a molding device for molding a three-dimensional (3D) pattern on a first web. The molding device is, for example, an embossing device.

According to an aspect, the molding device comprises a first roller, or drum, rotatable about a respective axis, for example, anticlockwise, and a second roller, or drum, rotatable about a respective axis, for example, clockwise.

The drums of the molding device are positioned relative to each other to define a gap through which the first web passes and their axes are parallel.

According to an aspect, the drums of the molding device are provided, on their outside surfaces, with male and female portions shaped to match each other and to impart to the web the aforementioned 3D pattern or motif when the web passes through the gap.

According to an aspect, the web is molded by conveying it between the drums of the molding device.

The male and female portions are shaped according to the shape which the protrusions on the continuous web should have.

According to an aspect, the forming unit comprises an applicator device for applying the segments to the second web.

According to an aspect, the applicator device comprises a cutting device for cutting the segments from a continuous web.

According to an aspect, the applicator device comprises an anvil and a knife acting in conjunction with the anvil for cutting the segments from a continuous web.

According to an aspect, the knife cuts the second continuous web to form the segments.

According to an aspect, the segments are spaced, for example, using a slip and cut method on the anvil itself.

According to an aspect, the applicator device comprises a joining device for joining the segments downstream of the cutting device.

According to an aspect, the joining device comprises a welding drum, tangent to one of the drums of the molding device, to join the segments to the continuous web.

In an example, the segments pass from the anvil of the cutting device onto one of the drums of the molding device and are then welded by the welding drum.

In another example, the welding drum receives the segments from the cutting device, for example, retaining them by suction, and applies them to the continuous web.

According to an aspect, the welding drum and the drum of the molding device are configured to weld the segments to the continuous web, for example, by thermal welding.

BRIEF DESCRIPTION OF THE DRAWINGS

The main features of the invention are more apparent from the detailed description which follows, with reference to the accompanying drawings which illustrate a preferred embodiment of the invention purely by way of non-limiting example, and in which.

DESCRIPTION OF THE PREFERRED EMBODIMENTS

Figures 1, 2, 3:
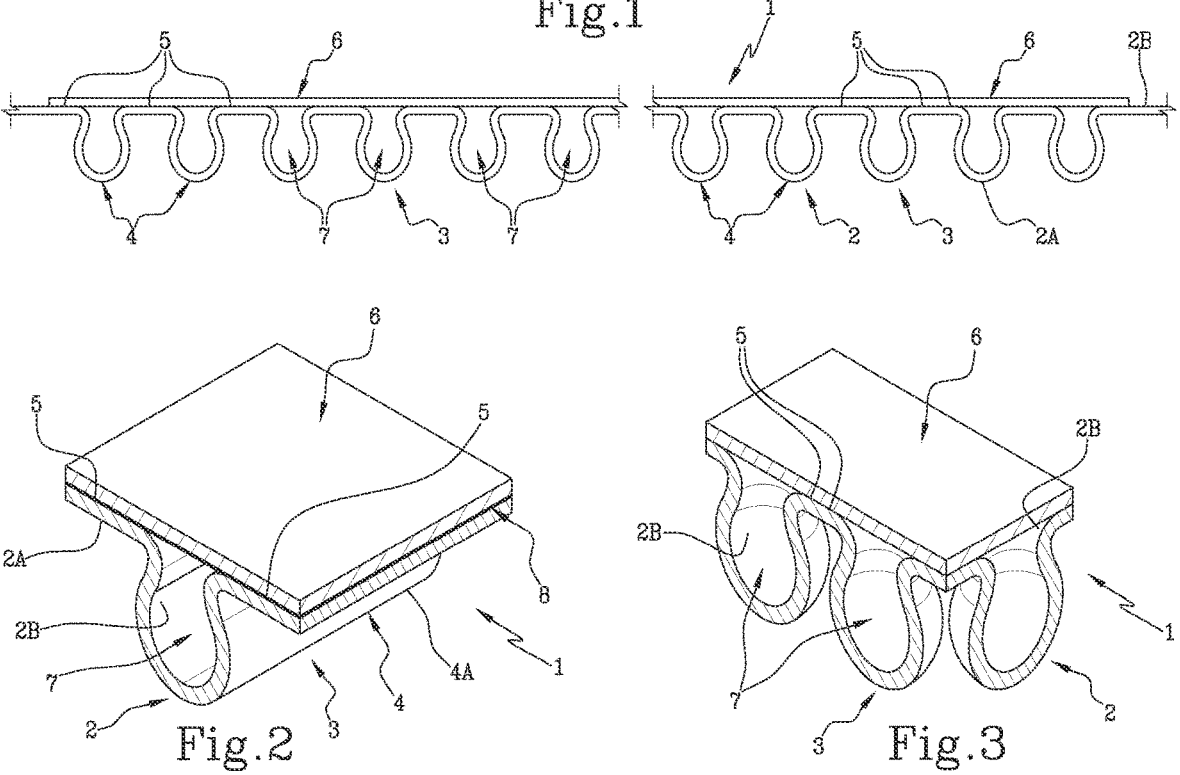
FIG. 1 illustrates a detail of a composite web according to the description in a schematic cross sectional view.
FIG. 2 illustrates a detail of a composite web according to the description in a schematic perspective view.
FIG. 3 illustrates a detail of a composite web according to the description in a schematic perspective view.

With reference to the accompanying drawings and, in particular, FIG. 1, the numeral 1 denotes a composite web according to the description.

Figure 4:
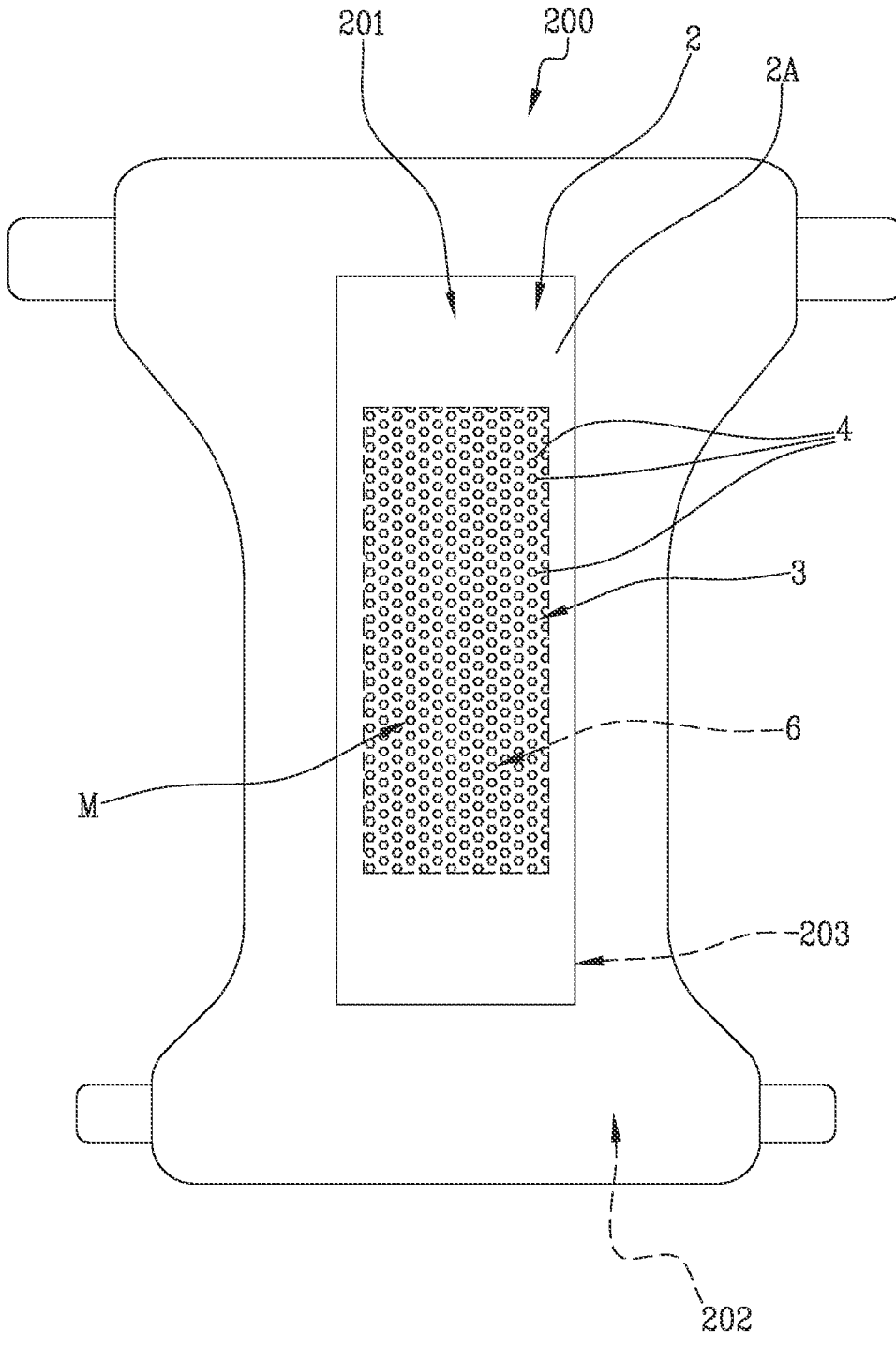
FIG. 4 illustrates an absorbent article according to the description in a schematic plan view.

The composite web 1 is preferably intended for the production of absorbent sanitary articles such as diapers, an example of which, labelled 200, is illustrated in FIG. 4.

The composite web 1, as explained in more detail below, allows making what are known as three-dimensional or 3D topsheets for absorbent sanitary articles such as diapers.

The composite web 1 comprises a first continuous web 2 having a first face 2A and a second face 2B.

As illustrated, the first web 2 comprises at least one molded or contoured portion 3; in the example of FIG. 1, two molded portions 3 are shown.

The contoured portion 3 is a web portion on which a pattern is stamped, that is, a portion of the first web with the molded pattern on it.

The molded portion 3 has at least one protrusion 4. The protrusion 4 is at least partly delimited by a base portion 5, outside the protrusion 4.

With reference to the accompanying drawings, the molded portions 3 are greatly scaled up in the illustrations so as to make it easier to understand the description.

The contoured portions 3 will constitute the 3D portions of the topsheet, provided normally to improve the comfort of the diaper.

The composite web 1 comprises a segment 6 of a second continuous web 16 joined to the second face 2B of the first web 2 at least at the base portion 5.

The composite web 1 has at least one cavity 7. The cavity 7 is delimited by the first web 2 and by the segment 6 at the molded portion 3.

In other words, the cavity 7 is delimited by the second face 2B of the first web 2 at the protrusion 4 and by the segment 6 of second web 16.

When the composite web 1 is used in an absorbent sanitary product, the wearer is in contact with the first face 2A of the first web 2.

Advantageously, the molded portion 3 allows ensuring the comfort of the wearer who comes into contact at least with the protrusion 4 present on the first face 2A.

The segment 6 keeps the molded portion 3 in the required shape.

In an embodiment, the first web 2 comprises non-woven fabric.

In an embodiment, the first web 2 comprises polymer fibers.

In an embodiment, the segment 6 comprises non-woven fabric.

In an embodiment, the segment 6 is a liquid acquisition and distribution layer (ADL).

Advantageously, applying an ADL allows acquiring the liquids from the upper layers and directing them towards an absorbent core, thereby increasing the efficiency of the absorbent sanitary product.

In an embodiment, the segment 6 comprises a layer of carded fibers.

In an embodiment, the segment 6 comprises cellulose fibers.

In an embodiment, the segment 6 is airlaid material.

In an embodiment, the segment 6 is spunlace material.

In an embodiment, the molded portion 3, on its first face 2A has a multiplicity of protrusions 4, delimited by a respective multiplicity of base portions 5 surrounding the protrusions 4.

In an embodiment, the composite web 1 comprises a segment 6 of a second web joined to the second face 2B of the first web 2 at least at the multiplicity of base portions 5. In this embodiment, the composite web 1 has a multiplicity of cavities 7, delimited by the first web 2 and the segment 6 at the molded portion 3.

The multiplicity of protrusions 4 defines a motif M. In other words, the multiplicity of protrusions 4 defines a pattern that will constitute the three-dimensional (3D) portion of the topsheet.

In an embodiment, the first web 2 is contoured, or molded along its full length.

In an embodiment, the composite web 1 comprises a discrete succession of segments 6 of second web 16.

The segments 6 keep the first web 2 in its molded shape at least at the segments 6 themselves.

The composite web 1 has a succession of molded portions 3, each kept in the required shape by the corresponding segment 6.

The first web 2 may lose the shape derived from molding in the zones where the segment 6 is not present. With reference to FIG. 1, the first web 2 is shown without protrusions at the ends of it.

In an absorbent article 200 which uses a segment of the composite web 1 as topsheet, this segment will have a molded portion 3 for the wearer's comfort, where the segment 6 is disposed and where this segment simultaneously keeps the molded portion 3 in the required shape and defines an ADL.

In an embodiment, the protrusions 4 of the first web 2 have a bubble shape, illustrated, for example, in FIGS. 3 and 4.

In an embodiment, the protrusions 4 of the first web 2 have a wavy shape, illustrated, for example, in FIG. 2.

In an embodiment, the waves molded on the first web 2 comprise waves with crests parallel to the main direction of extension of the first web 2.

In an embodiment, the waves molded on the first web 2 comprise waves with crests transverse to the main direction of extension of the first web 2.

The protrusions 4 of the first web 2 may have different shapes: for example, diamond, heart, oval, teardrop, elliptic, shamrock.

The first web 2 and the segments 6 of the second web 16 are joined, for example, by welding and/or adhesive.

In an embodiment, the molded portion 3 of the first web 2 and the segment 6 of the second web 16 are joined by welding, in particular, thermal welding or thermomechanical welding.

In an embodiment, the molded portion 3 of the first web 2 and the segment 6 of the second web 16 are joined by ultrasound welding.

In an embodiment, the composite web 1 comprises a layer of adhesive 8, visible, for example, in FIG. 2.

The layer of adhesive 8 is disposed between the web 2 and the segments 6, in particular, between the base portion 5 of the molded portions 3 of the first web 2 and the segment 6 of the second web 16.

This description also has for an object an absorbent article illustrated, for example, in FIG. 4 and denoted by the reference numeral 200.

The absorbent article 200, described only insofar as necessary for understanding this invention, essentially comprises: a topsheet 201, an impermeable backsheet 202 and an absorbent core 203 disposed between the topsheet 201 and the backsheet 202.

The topsheet 201 is the part of the article 200 which, in use, is in contact with the wearer.

The topsheet 201 comprises a segment of a composite web 1 according to the features described above.

The composite web 1 is cut to make a segment of composite web to be assembled in the article 200.

The segment of composite web comprises a segment of the first web 2 and at least one segment 6 of second web 16.

In an embodiment, the segment 6 of second web 16 is smaller in length than the segment of first web 2.

In an embodiment, the segment 6 of second web 16 is smaller in width than the segment of first web 2.

Figure 7A:
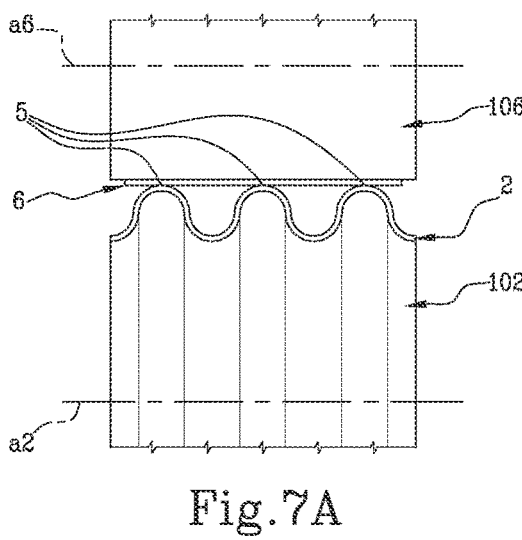
FIG. 7A illustrates a detail of a unit for the production of a composite web according to the description in a schematic view.
Figures 7B, 8:
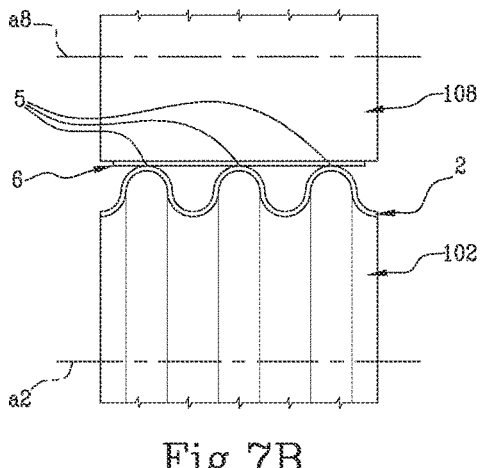
FIG. 7B illustrates a detail of a unit for the production of a composite web according to the description in a schematic view.
FIG. 8 illustrates an absorbent article according to the description in a schematic cross sectional view.

As illustrated, for example, in FIG. 8, the segment 6 of second web 16, included in the composite web 1, is disposed between the first web 2 (included in the composite web 1) and the absorbent core 203.

This description has for an object a method for the production of a composite web 1. The composite web 1 is preferably used for making absorbent sanitary articles such as, for example, the article 200.

The method comprises a step of feeding a first continuous web 2.

The method comprises a step of molding at least one portion of the first continuous web 2 to obtain at least one molded portion 3 having at least one protrusion 4, delimited at least partly by a base portion 5.

Preferably, the method, in particular, the step of molding, comprises a step of embossing the first continuous web 2 along its entire length. By "embossing" is meant stamping or molding a 3D pattern on the first web 2.

The method used to mold the first web 2 is commonly known as embossing.

Advantageously, making protrusions 4 on the first web 2 allows enhancing the comfort of the wearer in contact with the first web 2.

The method comprises a step of joining at least one segment 6 of a second web 16 to the first continuous web 2 at least at the base portion 5 to delimit at least one cavity 7 between the first continuous web 2 and the segment 6 at the at least one molded portion 3.

The segment 6 is joined to the first web 2 at the base portions 5 on the side opposite the protrusions 4 so as to also define the cavities 7.

In an embodiment the method comprises a step of feeding, cutting and spacing a second continuous web 16 to obtain segments 6 of second web 16.

The web segments can be cut and spaced from each other to obtain discrete components using a method known as slip and cut, whereby the segments are cut and allowed to slide.

In an embodiment, the step of joining at least one segment 6 of a second web 16 to the first continuous web 2 comprises a step of welding the segments 6 of second web 16 to the first continuous web 2.

In an embodiment, the step of welding the segment 6 to the first web 2 is performed by ultrasound welding.

In an embodiment, the step of joining at least one segment 6 of a second web 16 to the first continuous web 2 comprises a step of disposing a layer of adhesive 8 between the segments 6 of the second web and the first web 2.

Joining the segments 6 of the second web 16 to the first web 2 allows fixing and keeping, at least at the segments 6, the 3D pattern that has been imparted to the first web 2.

In a preferred embodiment, the first web 2 is molded with the pattern M along its full length and a succession of suitably sized and spaced segments 6 is then applied to it. The segments 6 are applied at the base portions 5 on the side opposite the protrusions 4 in a zone in which the molded portion 3 is defined and where the second segment 6 is and preferably defines an acquisition and distribution layer.

This description has for an object a forming unit 100 for making, for example, composite webs like the web 1.

The unit 100 comprises a molding device 101 for molding the 3D pattern on the first web 2. The device 101 is of a type substantially known in the trade and is also called embossing device.

Figure 5A:
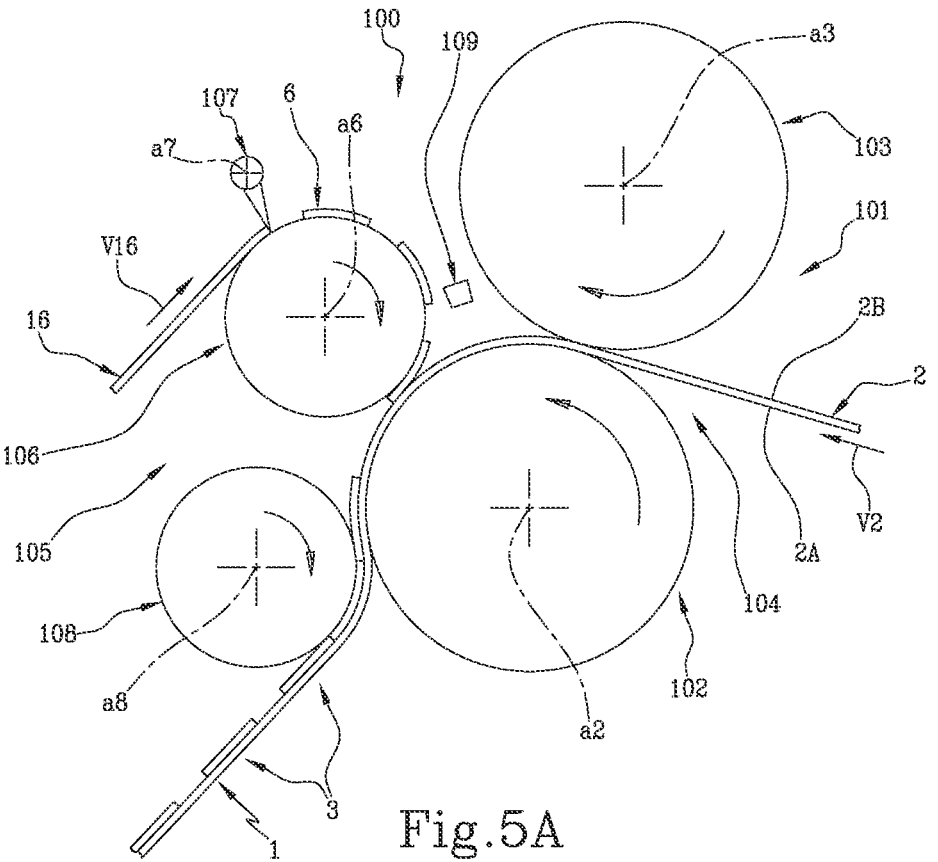
FIG. 5A illustrates a unit for the production of a composite web according to the description in a schematic front view.
Figure 5B:
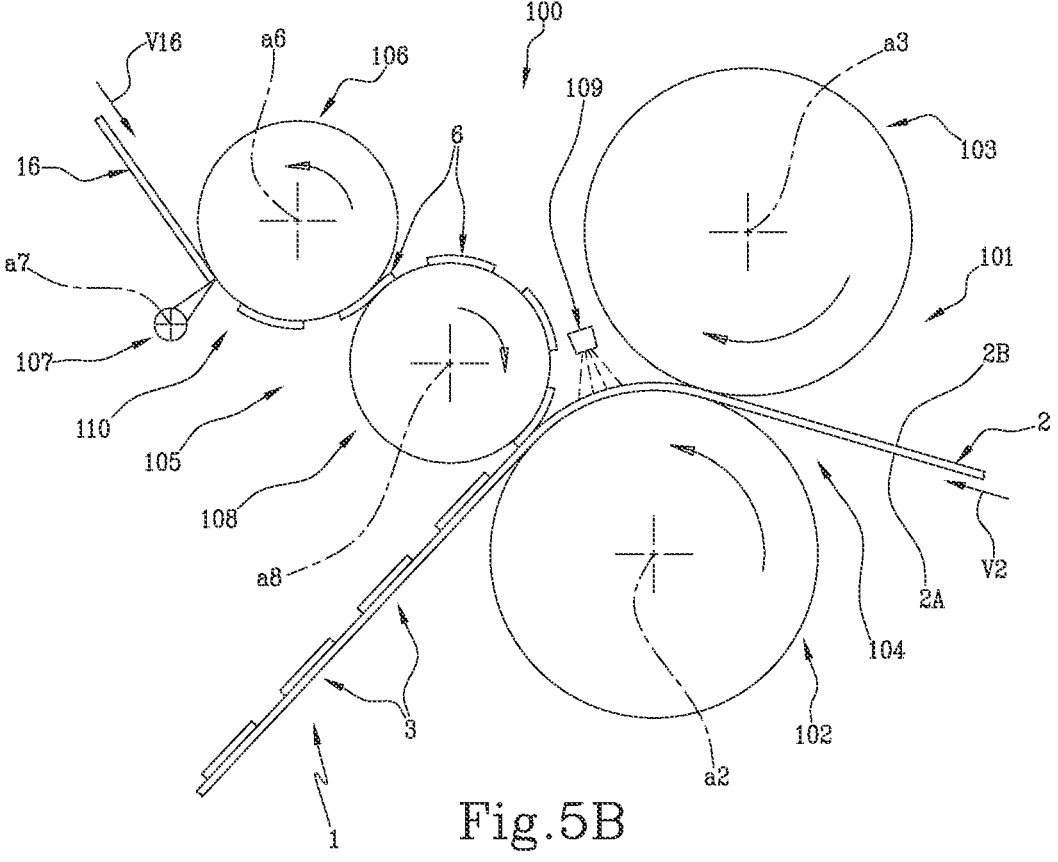
FIG. 5B illustrates a unit for the production of a composite web according to the description in a schematic front view.

In the examples illustrated in FIGS. 5A and 5B, the device 101 comprises a first roller or drum 102, rotatable about an axis a2 in anticlockwise direction, and a second roller or drum 103, rotatable about an axis a3, parallel to a2, in clockwise direction, positioned relative to each other to define a gap 104 through which the first web 2 passes; for simplicity, the rollers 102 and 103 are considered to be substantially tangent.

In an embodiment, the drum 102 and the drum 103 are provided, on their cylindrical outer surfaces, with male and female portions, respectively, which are shaped to match each other and to impart the aforementioned 3D pattern or motif to the first web 2.

The first web 2 is molded by conveying it between the drums 102, 103.

The male-female portions allow making the protrusions 4 on the first web 2.

The male and female portions are shaped according to the shape which the protrusion 4 should have.

Figure 6:
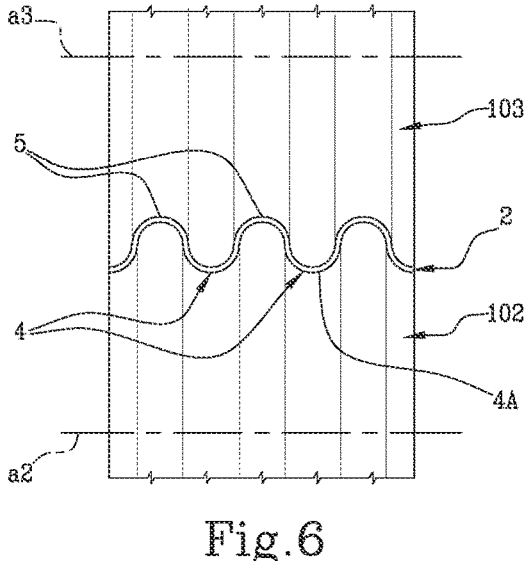
FIG. 6 illustrates a detail of a unit for the production of a composite web according to the description in a schematic view.

In FIG. 6, for example, the drums 102 and 103 are shaped to impart to the first web 2 wavy protrusions 4 where the crests 4A are parallel to the main directions of extension of the first web 2.

In an embodiment, the drum 103 is patterned and the drum 102 acts as anvil.

The first web 2 advances in a direction V2 through the gap 104 in such a way that the outside surfaces of the drums 102, 103 act in conjunction to engage the first web 2 and to impart the 3D pattern thereto.

Downstream of the molding device 101, the forming unit comprises an applicator device 105 for applying the segments 6.

In an embodiment, the applicator device 105 comprises a cutting device 110 to obtain the segments 6 from a continuous web 16.

In an embodiment, the cutting device 110 comprises an anvil 106, preferably in the form of a drum that is rotatable clockwise about an axis a6, and a rotary knife 107 that is rotatable anticlockwise about an axis a7, as illustrated in the example of FIG. 5A, and acting in conjunction with the anvil 106 to cut the segments 6 from a web 16.

The knife 107 cuts the second continuous web 16 to form the segments 6 which are suitably spaced, for example on the drum 106 itself with a known slip and cut method not further described.

In an embodiment, illustrated in the example of FIG. 7A, the drum 106 is tangent to the drum 102 to transfer the segments 6 onto the web 2 being fed by the drum 102.

The segments 6 are, for example, held by suction on the web 2 being fed by the drum 102.

The applicator device 105 comprises a joining device for joining the segments 6 to the web 2.

In an embodiment, the joining device comprises a welder which, in the example illustrated in FIG. 5A, comprises a welding drum 108 that is rotatable about an axis a8, clockwise in the example illustrated, disposed downstream of the drum 106 in the feed direction V16 of the web 16.

The drum 108 is tangent to the drum 102 and allows carrying out the step of joining the segments 6 to the first web 2, that is to say, joining the segments 6 to the base portions 5, as illustrated schematically in FIG. 7B.

In an embodiment, the drum 108 and the drum 102 are configured to weld the segments 6 to the web 2, for example by ultrasound welding.

In another embodiment, illustrated in the example of FIG. 5B, the drum 106 is tangent to the drum 108. The segments 6 are, in this case, transferred by the drum 106 to the drum 108 and welded onto the web 2 being fed by the drum 102 tangent to the drum 108.

In an embodiment, the applicator device comprises an adhesive dispenser 109.

The dispenser, preferably disposed downstream of the molding device 101, dispenses the layer of adhesive 8 to the web 2 so that the segments 6 can be joined to the first web 2 by the adhesive.

What is claimed is:

1. A method for production of a composite web for sanitary articles, comprising the following steps:
   feeding a first continuous web,
   molding the first continuous web to obtain at least one protrusion, the protrusion being delimited at least partly by a base portion,
   feeding a second continuous web,
   cutting the second continuous web into a plurality of individual segments,
   spacing apart the segments
   joining the spaced apart segments to the first continuous web at least at the base portion to delimit at least one cavity between each of the segments and the first continuous web.

2. The production method according to claim 1, wherein the step of joining the segments to the first continuous web comprises a step of welding each of the segments to the first continuous web at least at the base portion.

3. The production method according to claim 1, wherein the step of joining the segments to the first continuous web comprises a step of holding each of the segments on the first continuous web.

4. The production method according to claim 1, wherein the step of joining the segments to the first continuous web comprises a step of disposing a layer of adhesive between each of the segments and the first continuous web.

5. The production method according to claim 1, wherein the step of molding the first continuous web comprises a step of molding the first continuous web along a full length thereof, the step of joining the segments to the first continuous web defining a molded portion at least at each of the segments.

6. The production method according to claim 5, wherein the step of joining the segments to the first continuous web comprises a step of joining a discrete succession of the spaced apart segments to the first web, each of the segments of the discrete succession defining a corresponding molded portion in the composite web.

* * * * *